US006458565B1

(12) United States Patent
Cunningham et al.

(10) Patent No.: US 6,458,565 B1
(45) Date of Patent: Oct. 1, 2002

(54) METHOD FOR PRODUCING A HETEROLOGOUS SECRETED PROTEIN FROM CHINESE HAMSTER OVARY CELLS GROWN ON MICROCARRIERS

(75) Inventors: Mark Cunningham, Kennett Square, PA (US); Tom Iley, Franklin, MA (US)

(73) Assignee: Applied Research Systems ARS Holding N.V., Curacao (AN)

( * ) Notice: Subject to any disclaimer, the term of this patent is extended or adjusted under 35 U.S.C. 154(b) by 0 days.

(21) Appl. No.: 09/654,353

(22) Filed: Sep. 1, 2000

Related U.S. Application Data

(60) Provisional application No. 60/152,311, filed on Sep. 3, 1999.

(51) Int. Cl.[7] .......................... C12P 21/04; C12P 21/06; C12N 5/00; C12N 5/06
(52) U.S. Cl. .................... 435/70.3; 435/69.1; 435/70.1; 435/325; 435/326
(58) Field of Search ................. 435/69.1, 325, 435/326, 320.1, 70.1, 70.3, FOR 100, FOR 104

(56) References Cited

U.S. PATENT DOCUMENTS 5,219,752 A    6/1993   Takazawa et al.

FOREIGN PATENT DOCUMENTS

| EP | 0 338 716 | 10/1989 |
| EP | 0 584 788 | 3/1994 |
| EP | 0 679 717 | 11/1995 |
| WO | 97 05240 | 2/1997 |
| WO | 98 16629 | 4/1998 |

OTHER PUBLICATIONS

Xie et al., "Integrated approaches to the design of media and feeding strategies for fed–batch cultures of animal cells", *Trends in Biotechnology*, (1997) vol. 15, No. 3, pp. 109–113.

Primary Examiner—Bradley L. Sisson
(74) Attorney, Agent, or Firm—Browdy and Neimark

(57) ABSTRACT

The present invention relates to a method for producing a heterologous secreted protein from transformed CHO cells grown on microcarriers in a serum-free cell culture medium. This method avoids a production lag phase when switching from a serum-containing to a serum-free environment, a problem observed in the mammalian adherent cell culture production of secreted proteins.

13 Claims, 3 Drawing Sheets

Day 4

Day 6

Day 10

Day 1

Day 3

Day 6

Day 10

METHOD FOR PRODUCING A HETEROLOGOUS SECRETED PROTEIN FROM CHINESE HAMSTER OVARY CELLS GROWN ON MICROCARRIERS

This application claims the benefit of U.S. provisional application No. 60/152,311, filed Sep. 3, 1999.

BACKGROUND OF THE INVENTION

1. Field of the Invention

The present invention relates to a method for producing a secreted protein in mammalian adherent cell culture.

2. Description of the Related Art

The majority of industrial production processes that utilize Chinese hamster ovary (CHO) host cells use cell lines adapted to grow in suspension, e.g., t-PA (Werner et al., 1993 and Lubiniecki et al., 1994), for which serum-free medium have been available for the last 10 years (Gorfien et al., 1991). However, an alternative strategy for CHO cell culture is to support attached cell growth where cells adhere to a matrix, e.g., a microcarrier (Kadouri, 1994). CHO cells can grow successfully on such supports, and industrial processes have been developed utilizing CHO microcarrier cultures, e.g., Puregonâ (Olijve et al., 1996).

The adherent growth of CHO cells on microcarriers is usually accomplished by supplying serum to the culture, in the form of fetal bovine serum (FBS) (Xiao et al., 1994; Clark et al., 1981; Nikolai et al., 1992; Asselbergs et al., 1992; Levin et al., 1992; Watson et al., 1994 and Ohlson et al., 1994). This complex culture medium supplement contains the necessary attachment and growth factors required to promote the adherent phenotype, e.g., fibronectin, laminin (Zaworski et al., 1993 and Nilsson, 1989). Without the presence of serum, it has been reported that some cell lines will not grow on microcarriers (Schmid et al., 1992), or that the absence of serum is detrimental to product formation (Teige et al., 1994). Although serum-free adherent growth of CHO cells has been accomplished using a basal medium supplemented with insulin, transferrin and selenium (Gasser et al., 1985), this growth was obtained in the very passive environment of a T-flask, an environment that is known to differ significantly from the environment encountered in attached growth on microcarriers in a bioreactor (Cherry et al., 1985).

For microcarrier-based industrial processes, cells are usually fed (via continuous perfusion) culture medium supplemented with serum until the cells fill the available surface area provided by the microcarrier (the growth phase). The perfused medium is then switched to a different medium, usually one that is a serum-free formulation, as cells at this point are not dividing and can rely on the existing extracellular matrix to support their attachment. It is during this second phase (the production phase) that conditioned medium is collected for recovery and purification of the recombinant protein. However, in such a two-phase system, the switch from growth to production can lead to a dramatic cellular response, such as cell loss and decreased volumetric productivity of recombinant protein (Cosgrove et al., 1995). Alternatively, a lag phase can occur when the cells respond to the dramatic switch in environment, which then results in a period of low recombinant protein productivity until the cells are able to recover.

Citation of any document herein is not intended as an admission that such document is pertinent prior art, or considered material to the patentability of any claim of the present application. Any statement as content or a date of any document is based on the information available to applicant at the time of filing and does not constitute an admission as to the correctness of such a statement.

SUMMARY OF THE INVENTION

It is an object of the present invention to avoid the problems and difficulties encountered in the prior art as discussed above.

The present invention provides a method for producing a heterologous secreted protein from transformed CHO cells grown on microcarriers in a serum-free cell culture medium. This method has the advantage of overcoming the problem of a production lag phase observed when switching from a serum-containing to a serum-free environment.

DETAILED DESCRIPTION OF THE INVENTION

Figure 1:
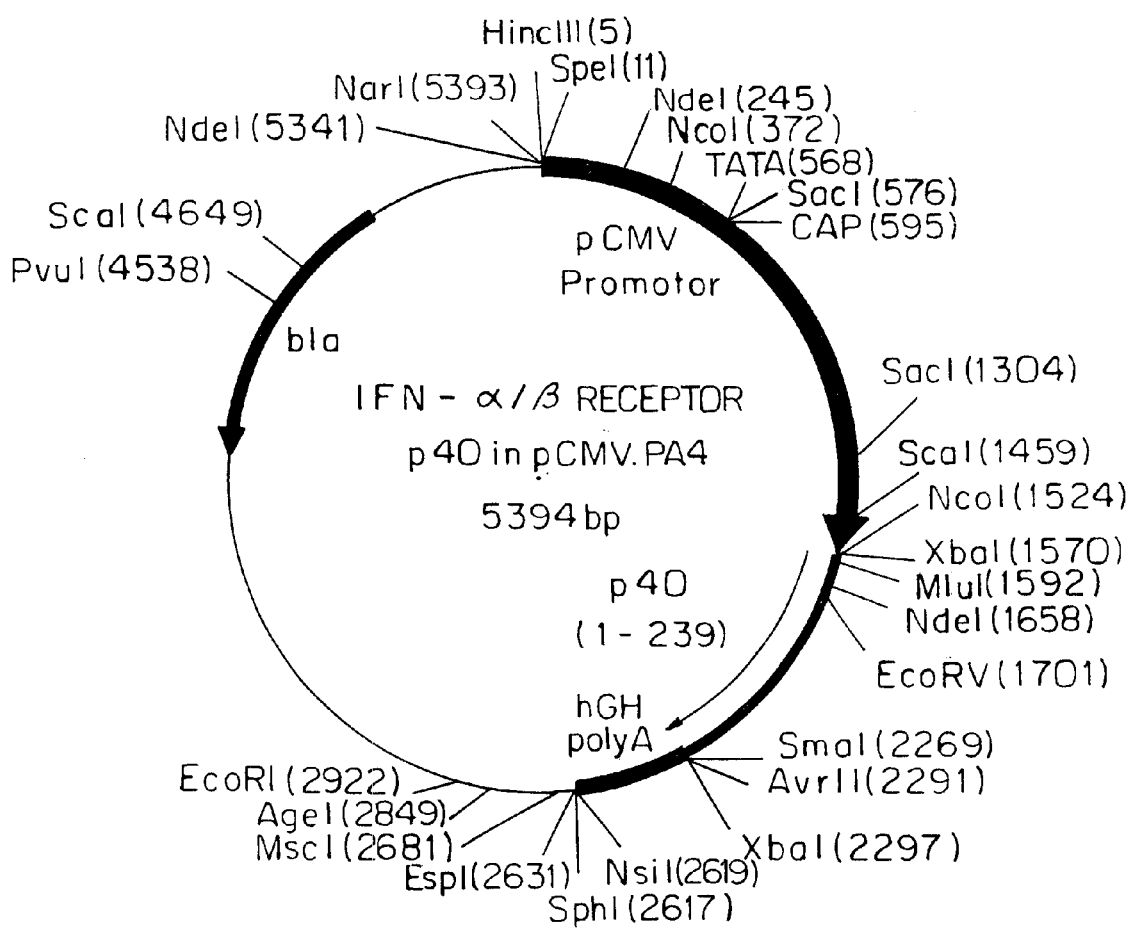
FIG. 1 shows the schematic representation of IFN $\alpha/\beta$ receptor p40 in pCMV.PA4.

The present invention is based on the development of a serum-free feeding strategy for growing CHO cells on microcarriers that overcomes the requirement for serum to promote an adherent cell phenotype. This serum-free feeding strategy according to the method of the present invention significantly improves the recovery of the desired secreted protein product by eliminating the lag phase associated with serum-removal, i.e., switching from a serum-containing to a serum-free environment.

The method for producing a heterologous secreted protein from CHO cells grown on microcarriers according to the present invention involves inoculating a cell bioreactor containing microcarriers as a solid support for adherent cell growth with an inoculum of CHO host cells transformed to express a heterologous secreted protein. While not absolutely necessary, the inoculated cells are preferably grown without perfusion in a serum-containing cell culture medium, such as DMEM/F12 supplemented with 5% fetal bovine serum (FBS), for a period of about one to three days, preferably about two days. After about two days, i.e., 48 hours, the cells are then fed via perfusion with a feed of a serum-free cell culture medium, which is preferably DMEM/F12 (catalogue no. 1330-032, Gibco BRL, Gaithersburg, Md.) supplemented with IFCSTE (an acronym for Insulin, Ferric Citrate, Selenium, and Trace Elements, the formulation of which is shown in Table 1 below), at an initial feed flow rate in the range of about 0.1 to 0.4 volume/volume/day (v/v/d) before increasing the feed rate of serum-free cell culture medium in stages over about a six to ten day period, preferably seven to nine days, until a feed flow rate of about 1 to 3.5 v/v/d is reached to produce and secrete the desired heterologous secreted protein from the culture CHO cells into the culture medium. The production and secretion of the desired heterologous secreted protein is maintained after the final feed flow rate is reached by continuous perfusion of serum-free culture medium supplemented with IFCSTE. The desired heterologous protein produced and secreted into the serum-free culture medium can be readily recovered and purified using conventional recovery and purification techniques well-known to those of skill in the art.

TABLE 1

Working Concentration of IFCSTE Supplement in Cell Culture Medium

| | | |
|---|---|---|
| 1) Insulin | | 1 mg/L |
| 2) Ferric Citrate | | 12.24 mg/L |
| 3) Sodium Selenium | | 68 µg/L |
| 4) Trace Metals A$^{16}$, 1000x (Gibco BRL catalogue #99–182) diluted 1:1000 for working concentration in micrograms per liter | | |
| CuSO$_4$.5H$_2$O | | 1.60 |
| ZnSO$_4$.7H$_2$O | | 863.00 |
| Selenite.2Na | | 17.30 |
| Ferric Citrate | | 1155.10 |
| 5) Trace Metals B$^{16}$, 1000x (Gibco BRL catalogue #99–175) diluted 1:1000 for working concentration in micrograms per liter | | |
| MnSO$_4$.H$_2$O | | 0.17 |
| NaSiO$_3$.9H$_2$O | | 140.00 |
| Molybdic Acid, Ammonium Salt | | 1.24 |
| NH$_4$VO$_3$ | | 0.65 |
| NiSO$_4$.6H$_2$O | | 0.13 |
| SnCl$_2$ (anhydrous) | | 0.12 |
| 6) Trace Metals C$^{16}$, 1000x (Gibco BRL catalogue #99–176) diluted 1:1000 for working concentration in micrograms per liter | | |
| AlCl$_3$.6H$_2$O | | 1.20 |
| AgNO$_3$ | | 0.17 |
| Ba(C$_2$H$_3$O$_2$)$_2$ | | 2.55 |
| KBr | | 0.12 |
| CdCl$_2$ | | 2.28 |
| CoCl$_2$.6H$_2$O | | 2.38 |
| CrCl$_3$ (amhydrous) | | 0.32 |
| NaF | | 4.20 |
| GeO$_2$ | | 0.53 |
| KI | | 0.17 |
| RbCl | | 1.21 |
| ZrOCl$_2$.8H$_2$O | | 3.22 |

It will be appreciated by those of skill in the art that the initial feed flow rate and the period of time for increasing the feed flow rate in stages to the final feed flow rate can be varied depending on the size of the inoculum. In a preferred embodiment, an inoculum of about 2×10$^5$ cells/ml is used for a 4.8 liter cell bioreactor and the cells are cultured for about two days before perfusing with an initial feed of serum-free culture medium at an initial feed flow rate of about 0.2 v/v/d. The feed flow rate for continuous perfusion of the adherent cell culture in the preferred embodiment is increased on day 3 to about 0.3 v/v/d, on day 4 to about 0.5 v/v/d, on day 5 to about 0.8 v/v/d, on day 6 to about 1.2 v/v/d, on day 7 to about 1.5 v/v/d, until a final flow rate of about 2.0 v/v/d is reached on day 8. As will be further appreciated by those of skill in the art given the guidance provided by the preferred embodiment according to the present invention, if the inoculum size is larger, then the initial feed flow rate may need to be higher and the period of time for increasing the flow rate may also need to be varied accordingly. The final feed flow rate can be between 1 to 3.5 v/v/d, but it is preferably about 2 v/v/d, such as in the range of about 1.5 to 2.5 v/v/d.

Although the method of the present invention can be generally applicable to the production and secretion of heterologous secreted proteins in CHO cells, where the term "heterologous secreted protein" is meant to be a secreted protein not endogenous to CHO cells, the preferred embodiment, as exemplified in the Example, is soluble interferon α/β receptor (sIFNAR2). Soluble human IFNAR2 is a glycosylated protein which binds both α and β interferon and its existence as a soluble form of the IFNα/β receptor offers the possibility of using the receptor therapeutically as an IFN antagonist.

The solid support on which adherent CHO cells are grown is preferably Cytopore 2 microcarriers (Amersham Pharmacia Biotech, Piscataway, N.J.), which are microcarriers with a cross-linked cotton cellulose matrix, a hydrophilic coating of DEAE, a charge density of 1.8 meq/g, and an average pore diameter of 30 µm. However, other suitable microcarriers known in the art for use in adherent cell culture can also serve as an alternate solid support for adherent growth of CHO cells.

The preferred serum-free cell culture medium is DMEM/F12 supplemented with IFCSTE.

Having now generally described the invention, the same will be more readily understood through reference to the following examples, which are provided by way of illustration and are not intended to be limiting of the present invention.

EXAMPLE 1

Clonal CHO cell lines, expressing recombinant soluble human IFN α/β Receptor (IFNAR2), were isolated and characterized. Two potential clones have been selected for further evaluation in a 100 population doubling stability study. Based on IFNAR2 expression levels and mRNA analysis, the following clones were selected from a panel of clones. CHO-IFNR1-1-50 had the highest specific productivity with a pod of 34.48. CHO-IFNR1-1-31 (CHO clone 1-1-31) had the highest volumetric productivity expressing 18.71 µg/ml in a T75 flask over a 24 h period. Both clones exhibited a single major mRNA species when examined by Northern Blot Analysis.

Methods

Vector Construction pCEV9-QM27 plasmid DNA containing soluble human IFN α/β receptor cDNA from Dr. Rubinstein was used as template for PCR amplification. A pair of PCR primers were used to amplify human IFN α/β receptor cDNA from the ATG start codon of the signal peptide to the TAG stop codon. A XbaI site was included in both primers. PCR was performed under standard conditions for 25 cycles. After gel purification and XbaI digestion, a 730 bp PCR product was ligated into XbaI digested, CIP-treated pCMV.PA4 expression vector. XbaI and NdeI digestions were used to screen the MC1061 transformants. The pCMV.PA-hIFN α/β receptor clone 11 was checked by restriction enzyme digestions and DNA sequence analysis. In the signal peptide region, a phenylalanine was found instead of valine at amino acid position 10 which is different from the published sequence (Rubinstein, 1994). The same change was found by Dr. Rubinstein in his original soluble form cloning construct.

Transfection and Selection in CHO Cells

CHO-DUKX cells were co-tranfected with the h IFN α/βR CMV.PA4 construct (50 μg) and with the Dα construct (10 μg) at a 5:1 ratio by routine $CaPO_4$ precipitation method. The Dα expression vector contains a dihydrofolate reductase (DHFR) gene thereby permitting selection and amplification with the drug methotrexate (MTX). The transfection was designated IFNR1. Growth medium utilized before and immediately following transfection consisted of alpha MEM (+) medium (with deoxy-and ribonucleosides, Gibco BRL) supplemented with 10% certified fetal bovine serum (FBS, Gibco BRL) and 1% L-glutamine (Gibco BRL). Forty-eight hours after transfection, each plate was rinsed with phosphate buffered saline (PBS), at pH 7.0, and treated with 2 ml of 0.05% trypsin-0.53 mM EDTA solution (Gibco BRL) for four minutes at 37° C. The trysin was quenched by the addition of 8 ml of selection medium consisting of alpha MEM (−) medium (without deoxy- and ribonucleosides, Gibco BRL) supplemented with 10% dialyzed fetal bovine serum (dFBS, Gibco BRL), 1% L-glutamine (Gibco BRL), and 0.02 μM MTX (Sigma). Dissociated cells were resuspended, split at a ratio of 1:10, and seeded in ten P100 culture dishes. Plates were refed with fresh selection medium every 3 to 4 days.

Typically after 10–14 days, large colonies form during selection. Plates were then trypsinized to redistribute the cells as pools so that a monolayer culture could form without overgrowth of localized areas. Once plates reached 80% confluence, they were refed with fresh selection medium. Twenty-four hours later, a sample of the supernatant was taken for expression analysis, cells were trypsinized, and counted using a hemacytometer. Two vials containing 1 to 3 million cells were cryopreserved in selection medium containing 10% dimethylsulfoxide (DMSO, Sigma) for each of the ten pools. Medium samples were stored at −20° C.

Amplification of CHO-IFNR1 Cells

Because the Dα vector contained the DHFR gene, it was possible to attempt to amplify the expression of the CHO-IFNR1 cells. Following selection at 0.02 μM MTX, transfected cells were amplified in "pools" according to standard amplification schedule of 0.1 μM→0.5 μM→1.0 μM→5.0 μM MTX. After twenty-four hour expression samples were taken at the 0.02 μM MTX level, the remaining cells were used for amplification. At each amplification stage, one P100 dish for each pool, was seeded at $7\times10^5$ cells in alpha MEM (−) medium supplemented with 10% dialyzed fetal bovine serum (dFBS, Gibco BRL), 1% L-glutamine (Gibco BRL), and the appropriate MTX concentration (Sigma). Cells were maintained at each successive amplification step for at least seven to ten days.

Twenty-four hour expression determinations, where expression levels were calculated on a per cell basis, were taken at each amplification stage as follows. When cells reached approximately 70–80% confluence, the plates were refed with fresh culture medium (containing the appropriate MTX concentration). Twenty-four hours later, supernatants were sampled, cells were trypsinized, and total cell counts were determined. After expression determinations were performed, at each amplification stage, $7\times10^5$ cells were used to seed a P100 in medium containing the level of MTX for the next amplification stage and the remaining cells were cryopreserved in medium containing the appropriate drug concentration for the current amplification stage and 10% DMSO. All IFNAR2 quantitation was done using the soluble human IFNAR2 ELISA.

ELISA Protocol for Soluble Human IFN Receptor

Immulon IV plates from Dynatech were coated with monoclonal antibody anti-IFNAR2 34.1 ascites, diluted 1:5000 in 0.1% Tween 20 in PBS, pH 7.4 (PBS/T) at 100 μl per well for 2 hours at 37° C. Plates were rinsed twice with PBS/T. All washes were at room temperature (RT) using an Ultrawash Plus automated aspirator/washer from Dynatech.

Plates were blocked overnight at 4° C. with 200 μl per well of 1.0% BSA in PES/T. Plates may be stored, cold, in block, for up to seven days. They were washed three times with PBS/T before further use.

Standard and samples were diluted in PBS/T. The standard was affinity purified rhIFN α/β receptor, stored at −20° C. or thawed and kept at ° C. for no longer than one week. The receptor was unstable at low concentrations, so it was diluted to working concentrations just before use. The standard was used at 200, 100, 50, 25, 12.5 and 6.25 ng/ml and at 100 μl per well with each concentration being run in triplicate. The diluted samples were also used at 100 μl per well in duplicate (or triplicate, space permitting). Standards and samples were allowed to incubate for one hour at RT. Plates were washed three times in PBS/T.

Polyclonal rabbit anti-IFNAR2 serum was diluted 1:5000 in PBS/T. 100 μl per well was used for one hour at RT. Plates were washed three times with PBS/T.

Biotinylated anti-rabbit antibody (Vector BA-1000) was diluted 1:10000 in PBS/T. 100 μl per well was used for one hour at RT. Plates were washed three times with PBS/T.

ABC reagent (Vector ABC Elite kit) was prepared as follows: 1 drop of reagent A was added to 10 ml PBS/T and mixed by inversion. 1 drop of reagent B was added and mixed by inversion. This mixture was allowed to incubate a minimum of 30 minutes at RT, then was diluted to a final volume of no more than 50 ml just before use. 100 μl per well of diluted ABC was allowed to incubate thirty minutes at RT. Plates were washed three times in PBS/T.

100 μl per well of TMB Microwell Peroxidase Substrate (Kirkegaard & Perry Lab, Gaithersburg, Md.) was allowed to incubate in the dark five minutes, then 50 μl per well of 0.3 M sulfuric acid was added to stop color development.

Plates were read at 450 nm using a UV max kinetic microplate reader from Molecular Devices.

Cloning of CHO-IFNR1-1

Using the IFNAR2 ELISA, detectable levels of h-sIFNAR2 were only found at 0.5, 1.0 and 5.0 μM MTX for a small portion of the IFNR1 pools. Based on these results IFNR1-1, at the 1 μM level, was selected for cloning. One vial of the IFNR1-1 pool was thawed into a T75 flask containing 1 μM MTX medium. Cells were passaged to T75 flasks in DMEM/F12 containing 5% FBS and a limited dilution cloning was performed. Five 96 well plates were inoculated with 0.25, 0.5, and 1 cells/well. Cloning was performed in the absence of drug. All wells were inspected by microscopic observation to ensure a single cell per well. Any wells that contained multiple cells were eliminated. After at least 11 days of growth, colonies from 82 wells were transferred to 24-well plates. Once cells reached 50–70% confluence, volumetric productivies were determined using IFNAR2 ELISA. Only those clones with high expression levels (~50% of the total clones) were transferred to a T25 flask where 24 hr volumetric expression deteminations were performed. Two vials of each clone were cryopreserved in DMEM/F12 containing 5% FBS, 1% L-glutamine, and 10% DMSO.

Expression Confirmation of Clones Post-Thaw

One vial of each of the top fifteen expression was thawed and used to inoculate a T25 flask. Cells were then expanded to two T75 flasks where duplicate 24 hr expressions were performed and an additional ten vials were cryopreserved.

Northern Analysis of Clones

Total RNA was isolated directly from cells grown in a T-75 flasks using TRIzol Reagent (Gibco, BRL) following the manufacturer's recommended procedure. Total RNA, 5 micrograms per lane, was size-fractionated in agarose gels which contained formaldehyde as a denaturant. The RNA was then transferred by capillary blot to GENE SCREEN PLUS nylon membranes and hybridized to a $^{32}$P-labeled hIFNAR2 probe from a PCR fragment of the cDNA. The band signals were quantitated on the Betascope model 603; sizes were estimated from autoradiographs of the blots.

Results

Amplification

Samples were assayed by ELISA at all of the amplification stages. Only two pools, IFNR1-1 and IFNR1-6 were detectable at the 0.5 to 5.0 and 1.0 and 5.0 $\mu$M MTX levels respectively. All other expression levels were too low to detect.

TABLE 2

Summary of Volumetric ($\mu$g/ml) Production Rates During Amplification

| Pool | CHO-IFNR1 Amplification MTX Level ($\mu$M) | $\mu$g/ml |
| --- | --- | --- |
| IFNR1-1 | 0.5 | 5.58 |
| IFNR1-1 | 1.0 | 9.40 |
| IFNR1-1 | 5.0 | 8.94 |
| IFNR1-6 | 1.0 | 7.39 |
| IFNR1-6 | 5.0 | 4.87 |

The IFNR1-1 pool at 1 $\mu$M MTX level had the highest volumetric productivity, 9.40 $\mu$g/ml, and was chosen for cloning. The specific productivity of this pool was 5.99 pcd.

Expression confirmation of Clones Post-Thaw

TABLE 3

IFNR1-1 Clone Expression Confirmation

| Clone | $\mu$g/ml | pcd |
| --- | --- | --- |
| 50 | 14.42 | 34.48 |
| 44 | 9.77 | 25.22 |
| 31 | 18.71 | 19.33 |
| 4 | 10.60 | 19.12 |
| 45 | 5.87 | 17.61 |
| 61 | 10.17 | 16.53 |
| 60 | 15.75 | 16.35 |
| 37 | 5.03 | 16.22 |
| 70 | 11.85 | 14.32 |
| 13 | 6.83 | 10.19 |
| 38 | 4.06 | 8.59 |
| 36 | 4.39 | 5.99 |
| 24 | 6.02 | 5.01 |

TABLE 3-continued

IFNR1-1 Clone Expression Confirmation

| Clone | $\mu$g/ml | pcd |
| --- | --- | --- |
| 8 | 3.41 | 4.48 |
| 56 | 5.14 | 3.25 |

The highest expressing clone was IFNR1-1-50 with a specific productivity of 34.48 pcd. The highest expresser based on volumetric expression was IFNR1-1-31 (CHO clone 1-1-31) with an expression level of 18.71 $\mu$g/ml.

EXAMPLE 2

In this example, sIFNAR2 is the heterologous secreted protein that is produced and secreted in adherent CHO cell culture. IFNAR2 is the beta subunit of the Type I interferon receptor (IFNAR), which is a heteromultimeric receptor complex composed of at least two different polypeptide chains, designated alpha and beta. Like the beta subunit, the alpha subunit has been renamed and is also known as IFNAR1. sIFNAR2 is soluble and not membrane bound because it lacks at least the transmembrane domain IFNAR2. The two bioreactor runs of CHO cells capable of producing and secreting sIFNAR2 as presented below demonstrate a normal "classic" approach (bioreactor run #4) and a novel serum-feeding strategy according to the present invention (bioreactor run #12) directed to adherent cell culture.

Bioreactor Run #4 (Serum-containing Feeding Strategy)

CHO clone 1-1-31 (expresses sIFNAR2) was grown in DMEM/F12 supplemented with 5% FBS in T-flasks and roller bottles until enough cells had been generated to inoculate a 4.8 l bioreactor. Cells were then trypsinized from the rollers and used to inoculate a reactor containing 2 g/l Cytopore 2 microcarriers in 4.8 l DMEM/F12 supplemented with 5% FBS. After a 24 hr period a feed of DMEM/F12 supplemented with 5% PBS was initiated at a flow rate of 0.3 volumes feed medium/volume reactor/day (v/v/d). This feed rate was increased in stages over an 8 day period until a flow rate of 2 v/v/d was reached (i.e. 9.6 l/day) At production day 0 (run day 9), the feed medium was switched to DMEM/F12 supplemented with 1 mg/l recombinant insulin, about 12 mg/l ferric citrate, 0.0068 mg/l selenium and a 1× solution of trace elements (IFCSTE). The feed flow rate of about 2 v/v/d was maintained throughout the production period. Cell growth on microcarriers and sIFNAR2 production was monitored.

Bioreactor Run #12 (Serum-free Feeding Strategy)

CHO clone 1-1-31 (expresses sIFNAR2) was grown in DMEM/F12 supplemented with 5% FBS in T-flasks and roller bottles until enough cells had been generated to inoculate a 4.8 l bioreactor. Cells were trypsinized from rollers and used to inoculate a reactor containing 2 g/l Cytopore 2 microcarriers in 4.8 l DMEM/F12 supplemented with 5% FBS. After a 48 hr period, a serum-free feed of DMEM/F12 supplemented with IFCSTE was initiated at a flow rate of 0.2 volume/volume/day. This feed flow rate was increased in stages over an 8 day period until a flow rate of 2 volume/volume/day was reached. "Production day" in this system was linked to the initiation of the feed (run day 2), as this was not a "classic" two-phase protocol. Cell growth on microcarriers and sIFNAR2 production was monitored.

Results

Figure 2:
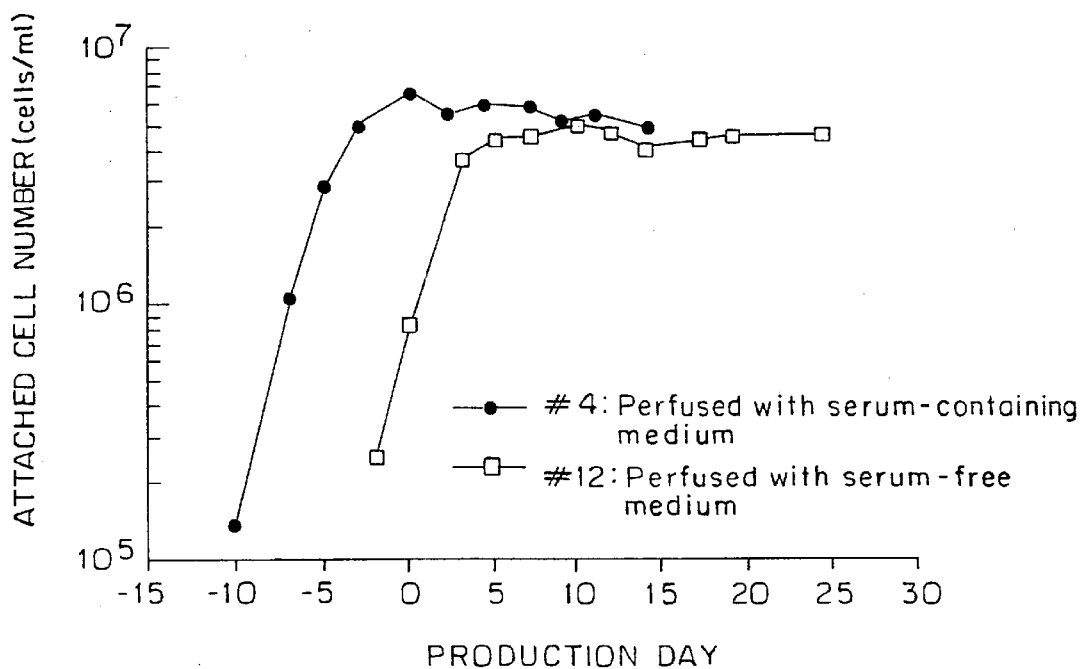
FIG. 2 shows the cell growth of CHO clone 1-1-31 on Cytopore 2 microcarriers fed with either serum-containing medium (bioreactor run #4 is fed with DMEM/F12 supplemented with 5% fetal bovine serum (FBS)) or serum-free medium (bioreactor run #12 fed with DMEM/F12 supplemented with IFCSTE).

As shown in FIG. 2, the rate of cell division and saturation density in both bioreactor runs #4 and #12 were comparable.

Cells fed with a serum-containing formulation (run #4) increased from $1.4\times10^5$ cells/ml to $6.7\times10^6$ cells/ml (5.5 cell generations) and cells fed with the serum-free formation increased from $2.5\times10^5$ cells/ml to $5.1\times10^6$ cells/ml (4.4 cell generations).

Figure 3:
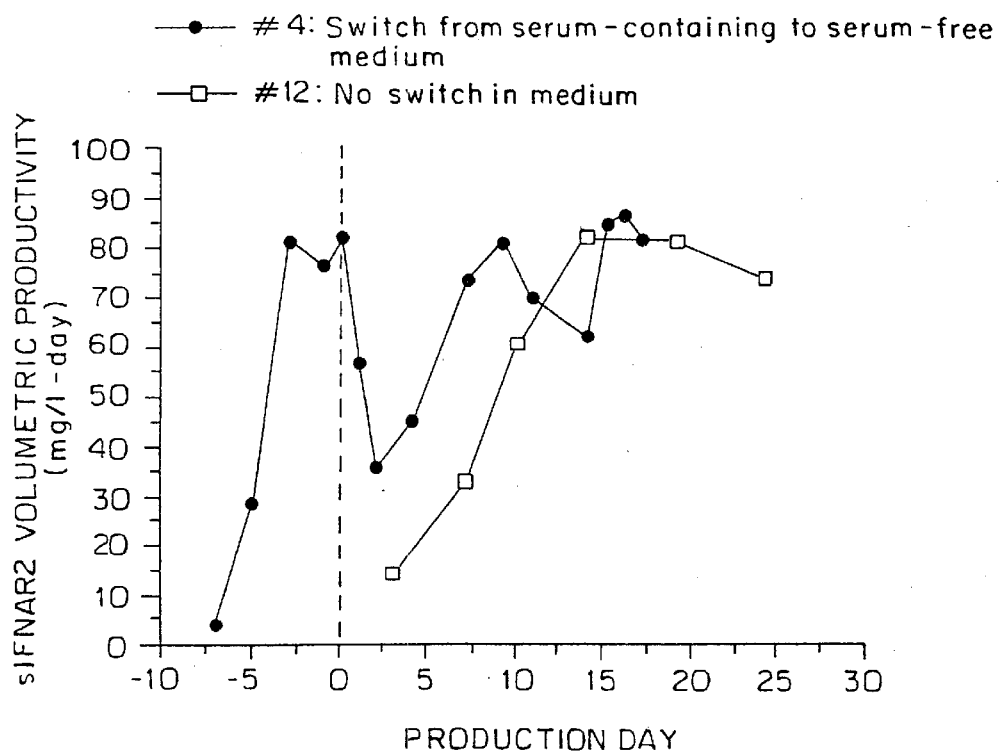
FIG. 3 shows the kinetics of soluble interferon $\alpha/\beta$ receptor (sIFNAR2) production in a two phase system, where there is a switch from serum-containing to serum-free medium, and in a system with a single feed and no switch in medium. Bioreactor run #4 was run as a two-phase system with a growth phase of DMEM/F12 supplemented with 5% FBS and a switch to a production phase of DMEM/F12 supplemented with IFCSTE. The switch is represented by the vertical dotted line at time 0. Bioreactor run #12 utilized a single feed medium of DMEM/F12 supplemented with IFCSTE.
Figure 4A:
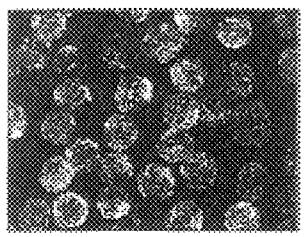
FIGS. 4A–4C show CHO cells (clone 1-1-31) growing on Cytopore 2 microcarriers on day 4 (FIG. 4A), day 6 (FIG. 4B), and day 10 (FIG. 4C) following feeding with the serum-containing formulation of DMEM/F12 supplemented with 5% FBS. Viable cells grown on the microcarrier is stained with a fluorescent stain. The day indicated in FIGS. 4A–4C are run days, i.e., days post bioreactor inoculation, and not production days.
Figure 4B:
Figure 4C:
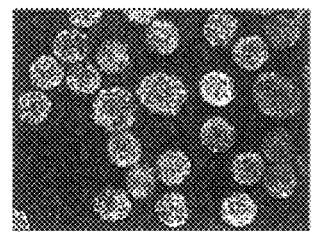
Figure 5A:
FIGS. 5A–5D show CHO cell (clone 1-1-31) growing on Cytopore 2 microcarriers on day 1 (FIG. 5A), day 3 (FIG. 5B), day 6 (FIG. 5C), and day 10 (FIG. 5D) following feeding with the serum-free formulation of DMEM/F12 supplemented with IFCSTE. Viable cells grown on the microcarrier is stained with a fluorescent stain. The day indicated in FIGS. 5A–5D are run days and not production days.
Figure 5B:
Figure 5C:
Figure 5D:

FIG. 3 illustrates the production kinetics of sIFNAR2 in bioreactor runs #4 and #12. Cells fed with DMEM/F12 supplemented with 5% FBS initially demonstrated a volumetric productivity of approximately 80 mg/1-day. However, upon switching to the serum-free formulation of DMEM/F12 supplemented with IFCSTE, a lag phase was observed where productivity fell to below 40 mg/1-day before recovering back to 80 mg/1-day after a 10 day period (run day 20). In contrast, cells fed from the start with DMEM/F12 supplemented with IFCSTE demonstrated no lag phase and reached 80 mg/1-day on run day 14.

The growth of CHO clone 1-1-31 on Cytopore 2 microcarriers fed with either a serum-containing or a serum-free formulation is monitored as shown in FIGS. 4A–4C and FIGS. 5A–5D, respectively, where viable cells, stained with a green fluorescent stain, are observed. FIGS. 4A–4C and FIGS. 5A–5D together illustrate that both the feeding strategies of bioreactor runs #4 and #12 support cell growth on microcarriers with increases in fluorescence observed over time.

Having now fully described this invention, it will be appreciated by those skilled in the art that the same can be performed within a wide range of equivalent parameters, concentrations, and conditions without departing from the spirit and scope of the invention and without undue experimentation.

While this invention has been described in connection with specific embodiments thereof, it will be understood that it is capable of further modifications. This application is intended to cover any variations, uses, or adaptations of the inventions following, in general, the principles of the invention and including such departures from the present disclosure as come within known or customary practice within the art to which the invention pertains and as may be applied to the essential features hereinbefore set forth as follows in the scope of the appended claims.

All references cited herein, including journal articles or abstracts, published or corresponding U.S. or foreign patent applications, issued U.S. or foreign patents, or any other references, are entirely incorporated by reference herein, including all data, tables, figures, and text presented in the cited references. Additionally, the entire contents of the references cited within the references cited herein are also entirely incorporated by references.

Reference to known method steps, conventional methods steps, known methods or conventional methods is not in any way an admission that any aspect, description or embodiment of the present invention is disclosed, taught or suggested in the relevant art.

The foregoing description of the specific embodiments will so fully reveal the general nature of the invention that others can, by applying knowledge within the skill of the art (including the contents of the references cited herein), readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance presented herein, in combination with the knowledge of one of ordinary skill in the art.

REFERENCES

Asselbergs et al., Scaled-up Production of Recombinant Human Renin in CHO Cells for Enzymatic and X-ray Structure Analysis, *J. Biotechnol.* 32:191–202 (1992)

Cherry et al., Physical Mechanisms of Cell Damage in Microcarrier Cell Culture Bioreactors, *Biotechnology and Bioengineering* 32:1001–1014 (1988)

Clark et al., Optimizing Culture Conditions for the Production of Animal Cells in Microcarrier Culture, *Annals New York Academy of Sciences* 33–46 (1981)

Cosgrove et al., Purification and Properties of Insulin Receptor Ectodomnain from Large-Scale Mammalian Cell Culture, *Protein Expression and Purification* 6:789–798 (1995)

Gasser et al., Long-Term Multiplication of the Chinese Hamster Ovary (CHO) Cell Line in a Serum-Free Medium, In Vitro *Cellular and Developmental Biology* 21(10) :588–592 (1985)

Gorfien et al., Growth and rDNA Protein Production in an Improved Serum-free Medium Formulation, *J. Cell Biol.* 115(3) Part 2, 358a (1991)

Kadouri, Cultivation of Anchorage-dependent Mammalian Cells and Production of Various Metabolites. Colloids and Surfaces B, *Biointerfaces* 2:265–272 (1994)

Levin et al., Purification of Recombinant Human Secretary Phospholipase A2 (Group II) Produced in Long-term Immobilized cell Culture, *Protein Expr. Purif.* 3 (1) 27–35 (1992)

Lubiniecki et al., Purified Protein Products of rDNA Technology Expressed in Animal Cell Culture, *Biologicals* 22:161–169 (1994)

Nikolai et al., Cultivation of Mammalian Cells on Macroporous Microcarriers, *Enzyme Microb. Technol.* 14:203–208 (1992)

Nilsson, Microcarrier Cell Culture, *Biotechnology and Genetic Engineering Reviews* 6(11):403–439 (1989)

Ohlson et al., Bead-to-Bead Transfer of Chinese Hamster Ovary Cells Using Macroporous Microcarriers, *Cytotechnology* 14:67–80 (1994)

Olijve et al., Molecular Biology and Biochemistry of Human Recombinant Follicle Stimulating Hormone, *European Society for Human Reproduction and Embryology* 372–382 (1996)

Rubinstein, *Cell*, 77:391–400 (1994)

Schmid et al., Repeated Batch Cultivation of rBHK Cells on Cytodex 3 Microcarriers: Antithrombin III, Amino Acid, and Fatty Acid Metabolic Quotients, *Appl. Microbiol. Biotechnol.* 38:328–333 (1992)

Teige et al., Problems with Serum-Free Production of Anti-Thrombin III Regarding Proteolytic Activity and Product Quality, *J. Biotechnol.* 34: 101–105 (1994)

Watson et al., Comparison of N-linked Oligosaccharides of Recombinant Human Kallikrein Produced by Chinese Hamster Ovary cells on Microcarrier Beads and in Serum-Free Suspension Culture, *Biotechnol. Prog.* 10(1) (1994)

Werner et al., Mammalian Cell Cultures, *Arzaneim.-Forsch./Drug Res.* 43(II):1134 (1993)

Xiao et al., High Density Cultivation of Genetically-engineered CHO Cell Lines With Microcarrier Culture Systems, *Chin. Med. Sci. J.* 9(2):71–74 (1994)

Zaworski et al., Serum-Free transfection and Selection in Chinese Hamster Ovary (CHO) Cells, *BioTechniques.* 15(5):863–866 (1993)

What is claimed is:

1. In a method for producing a heterologous secreted protein from Chinese Hamster Ovary (CHO) cells grown on microcarriers, comprising:

inoculating a cell bioreactor, containing microcarriers as a solid support for adherent cell growth and serum-containing cell culture medium, with an inoculum of CHO host cells transformed to express a heterologous secreted protein, wherein the inoculum was prepared by growing the transformed CHO host cells in serum-containing cell culture medium; and culturing the inoculated CHO host cells in adherent cell culture without perfusion of cell culture medium for a period of about one to three days prior to the initiation of feed;

the improvement, comprising:

initiating a feed of serum-free cell culture medium supplemented with insulin, ferric citrate, selenium and trace elements to the cell bioreactor via continuous perfusion;

increasing the feed flow rate of serum-free cell culture medium supplemented with trace elements in stages until a final feed flow rate in a range of about 1 to 3.5 volume/volume/day is reached to produce and secrete a heterologous protein from the CHO host cells into the serum-free cell culture medium, wherein initiating feed and increasing the feed flow rate are performed together over a six to ten day period; and culturing the CHO host cells in adherent cell culture at the final feed flow rate.

2. The method according to claim 1, wherein the period of culturing the inoculated CHO host cells is about 2 days.

3. The method according to claim 1, wherein the feed initiating step initiates a feed at a flow rate in the range of about 0.1 to 0.4 volume/volume/day of serum-free cell culture medium supplemented with insulin, ferric citrate, selenium and trace elements.

4. The method according to claim 3, wherein the feed is initiated at a feed flow rate in the range of about 0.2 to 0.3 volume/volume/day.

5. The method according to claim 3, wherein the feed is initiated at a feed flow rate of about 0.2 volume/volume/day.

6. The method according to claim 1, wherein the feed flow rate is increased in stages over about a seven to nine day period.

7. The method according to claim 1, wherein the feed flow rate is increased in stages over about an eight day period.

8. The method according to claim 1, wherein the final feed flow rate is in the range of about 1.5 to 2.5 volume/volume/day.

9. The method according to claim 1, wherein the final feed flow rate is about 2 volume/volume/day.

10. The method according to claim 1, further comprising a step of recovering the heterologous protein from the serum-free cell culture medium.

11. The method according to claim 1, wherein the heterologous protein is soluble interferon $\alpha/\beta$ receptor (sIFNAR2).

12. The method according to claim 1, wherein the microcarriers are Cytopore 2.

13. The method according to claim 1, wherein the serum-free cell culture medium is DMEM/F12.

* * * * *